(12) United States Patent
Moszner et al.

(10) Patent No.: US 10,667,993 B2
(45) Date of Patent: Jun. 2, 2020

(54) POLYMERIZABLE COMPOSITIONS BASED ON THERMALLY CLEAVABLE COMPOUNDS

(71) Applicants: Ivoclar Vivadent AG, Schaan (LI); Karlsruher Institut für Technologie, Karlsruhe (DE)

(72) Inventors: Norbert Moszner, Mauren (LI); Iris Lamparth, Grabs (CH); Kai Rist, Feldkirch (AT); Christoph Barner-Kowollik, Stutensee (CH); Alexander Schenzel, Karlsruhe (DE); Marcel Langer, Mühlhausen (DE)

(73) Assignees: Ivoclar Vivadent AG, Schaan (LI); Karlsruher Institute Für Technologie, Karlsruhe (DE)

( * ) Notice: Subject to any disclaimer, the term of this patent is extended or adjusted under 35 U.S.C. 154(b) by 106 days.

(21) Appl. No.: 15/743,731

(22) PCT Filed: Oct. 11, 2016

(86) PCT No.: PCT/EP2016/074305
§ 371 (c)(1),
(2) Date: Jan. 11, 2018

(87) PCT Pub. No.: WO2017/064042
PCT Pub. Date: Apr. 20, 2017

(65) Prior Publication Data
US 2018/0200155 A1   Jul. 19, 2018

(30) Foreign Application Priority Data
Oct. 13, 2015   (EP) .................................... 15189615

(51) Int. Cl.
*A61K 6/083* (2006.01)
*A61K 6/887* (2020.01)
*A61K 6/30* (2020.01)
*A61L 24/06* (2006.01)
*C08L 33/08* (2006.01)
*C08L 33/10* (2006.01)

(52) U.S. Cl.
CPC ............... *A61K 6/887* (2020.01); *A61K 6/30* (2020.01); *A61L 24/06* (2013.01); *C08L 33/08* (2013.01); *C08L 33/10* (2013.01); *C08L 2203/02* (2013.01)

(58) Field of Classification Search
CPC ..................................................... A61K 6/083
See application file for complete search history.

(56) References Cited

U.S. PATENT DOCUMENTS

| 2007/0142494 | A1  | 6/2007  | Kalgutkar et al. |
| 2007/0142498 | A1* | 6/2007  | Brennan ............. A61K 6/0023 523/118 |
| 2012/0226009 | A1* | 9/2012  | Jin ........................ A61K 6/083 526/313 |
| 2014/0329929 | A1  | 11/2014 | Moszner et al. |
| 2014/0371341 | A1  | 12/2014 | Moszner et al. |

OTHER PUBLICATIONS

Written Opinion of the International Searching Authority of PCT/EP2016/074305, dated Jan. 11, 2017, 6 pages.

* cited by examiner

*Primary Examiner* — Michael F Pepitone
(74) *Attorney, Agent, or Firm* — Ann M. Knab; Thad McMurray (57) ABSTRACT

The invention relates to a polymerizable composition which comprises a thermolabile polymerizable compound of Formula I:

A-[X-(T-X-Sp-X)$_p$-T-X-Q-(Z)$_n$]$_m$   Formula I, wherein T represents a thermolabile Diels-Alder or hetero-Diels-Alder group of the Formula

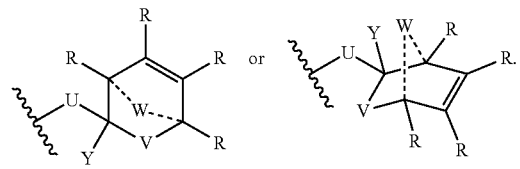

The invention also relates to the use of the polymerizable composition according to the present invention and the compounds of Formula I according to the present invention as polymerization resin or for the preparation of polymerization resins and polymerizates such as adhesives, composites, stereolithographic materials, shaped parts, duromers and mounting and fixing elements, and as dental material and for the preparation of dental materials such as adhesives, cements and filling composites.

25 Claims, 2 Drawing Sheets

POLYMERIZABLE COMPOSITIONS BASED ON THERMALLY CLEAVABLE COMPOUNDS

CROSS-REFERENCE TO RELATED APPLICATIONS

This application is a National Stage application of International patent application PCT/EP2016/074305 filed on Oct. 11, 2016, which claims priority to European patent application No. 15189615.6 filed on Oct. 13, 2015, the disclosures of which are incorporated herein by reference in their entirety.

FIELD OF THE INVENTION

The present invention relates to thermally cleavable compounds and the use thereof as cross-linking monomer components, in particular in polymerization resins and polymerizates such as adhesives, composites, stereolithographic materials, shaped parts, duromers as well as chemically reversible mounting and fixing elements and in particular in dental materials such as adhesives, cements and filling composites.

BACKGROUND OF THE INVENTION

Adhesive bonds that can be debonded again are increasingly important in various technological fields. Examples are the detachment of components within the framework of automated manufacturing processes, the repair of complex components with adhesively bonded subcomponents or the simplification of the separation of materials when recycling such components at the end of the product's life. The debonding of adhesive bonds can be achieved on demand by significantly reducing the strength of the adhesive bond layer e.g. by heating.

Thus, DE 198 32 629 A1 describes an adhesive system for forming reversible adhesive bonds based on polyurethanes, polyureas or epoxy resins, in which an additional component can be activated by introducing energy such that a degradation of the adhesive components takes place. For example, organic bases or acids which degrade the adhesive resin can be released from blocked precursors by introducing heat or radiation energy.

WO 2010/128042 A1 describes industrial adhesive compositions for debondable adhesive bonds for aircraft or motor vehicle construction which consist of a customary adhesive matrix and a particulate expansion material such as e.g. azodicarbonamide. The components are debonded by heating the adhesive bond at least to the expansion temperature of the expansion material.

In dentistry, the debonding of adhesive bonds is important among other things in orthodontics, where brackets which are adhesively bonded to the tooth surface to correct mal-occlusions must be removed again without damaging the tooth enamel after successful correction. Moreover, in case of repair or complete replacement of high-strength ceramic restorations or crowns, which are laborious to remove mechanically, cement bonds that can be easily softened or separated would be advantageous.

In connection with orthodontic applications, US 2007/0142498 A1 describes dental compositions which contain thermally controllable additives such as e.g. thermoplastic polymers.

US 2007/0142497 A1 describes dental compositions based on dimethacrylates with acid-labile tertiary carbonate groups and photoacids such as e.g. triarylsulfonium salts. These compositions can be photochemically cured using light in the visible range with suitable initiators such as, for instance, the bisacyl phosphine oxide Irgacure 819 (photobonding) and softened again by irradiation with UV light at increased temperature (photothermal debonding).

WO 2013/034777 A2 describes dental materials which contain polymerizable compounds with a thermolabile or photolabile group such as a thermolabile Diels-Alder group. However, it was found that these materials must be exposed to relatively high temperatures of typically more than 100° C. in order to bring about a sufficiently rapid softening.

SUMMARY OF THE INVENTION

It is an object of the invention to provide compositions which are storage-stable at room temperature and are polymerizable to form network polymers and can be thermally softened in a reversible manner in the polymerized state even at relatively low temperatures of in particular less than 100° C. and thus above all are suitable for the preparation of materials with self-healing or debonding-on-demand properties such as chemically reversible mounting and fixing elements as well as of dental materials such as adhesives, cements and filling composites.

BRIEF DESCRIPTION OF THE DRAWINGS

Other advantages, details and characteristics can be seen from the following description and drawings wherein.

DETAILED DESCRIPTION

This object is achieved according to the present invention by polymerizable compositions based on a thermolabile polymerizable compound of Formula I:

A-[X-(T-X-Sp-X)$_p$-T-X-Q-(Z)$_n$]$_m$  Formula I, in which

A represents an m-valent linear, branched or cyclic aliphatic or aromatic $C_1$-$C_{30}$ radical which can be interrupted by —O—, —S—, —CO—O—, —O—CO—, —CO—$NR^3$—, —$NR^3$—CO—, —O—CO—$NR^3$—, —$NR^3$—CO—O— or —$NR^3$—CO—$NR^3$—, or represents an oligomeric group with a molar mass of from 200 to 2000 g/mol, Q in each case independently is absent or represents an (n+1)-valent linear, branched or cyclic aliphatic or aromatic $C_1$-$C_{20}$ radical which can be interrupted by —O—, —S—, —CO—O—, —O—CO—, —CO—$NR^3$—, —$NR^3$—CO—, —O—CO—$NR^3$—, —$NR^3$—CO—O— or —$NR^3$—CO—$NR^3$—, Sp in each case independently represents a linear, branched or cyclic aliphatic or aromatic $C_1$-$C_{30}$ radical which can be interrupted by —O—, —S—, —CO—O—, —O—CO—, —CO—$NR^3$—, —$NR^3$—CO—, —O—CO—

$NR^3$—, —$NR^3$—CO—O— or —$NR^3$—CO—$NR^3$—, or represents an oligomeric group with a molar mass of from 200 to 2000 g/mol, T is selected in each case independently from U in each case independently represents $CH_2$, S, NH, O,
V in each case independently represents $CH_2$, S, NH, O,
W in each case independently is absent or represents $CH_2$, O, S or NH,
X in each case independently is absent or represents —O—, —S—, —CO—O—, —O—CO—, —CO—$NR^3$—, —$NR^3$—CO—, —O—CO—$NR^3$—, —$NR^3$—CO—O— or —$NR^3$—CO—$NR^3$—,
Y in each case independently represents H, $R^4$, aryl, heteroaryl, —CN, —$OR^4$, —$N(R^4)_2$ or —$P(O)(OR^4)_2$,
Z in each case independently represents a polymerizable group selected from vinyl groups, $CH_2$=$CR^1$—CO—O— and $CH_2$=$CR^1$—CO—$NR^2$—,
one of the groups R represents a bond and the remaining groups R independently represent H or a linear or branched $C_1$-$C_9$ alkyl radical,
$R^1$, $R^2$ and $R^3$ in each case independently represent H or a linear or branched $C_1$-$C_9$ alkyl radical,
$R^4$ in each case independently represents a linear or branched $C_1$-$C_9$ alkyl radical,
m can assume the values 2 to 6,
n in each case independently can assume the values 1, 2 or 3,
p can assume the values 0 to 10.

The indication that a radical can be interrupted by a group, such as for example —O—, is to be understood such that the group is inserted into the carbon chain of the radical, i.e. is bordered on both sides by carbon atoms. The number of these groups is therefore smaller than the number of carbon atoms by at least 1 and the groups cannot be terminal. According to the present invention, radicals which are not interrupted by the named groups are preferred.

Only those compounds which are compatible with the chemical valence theory are considered.

According to the present invention, compounds of Formula I are preferred in which independently of each other
U in each case independently represents S, NH or O and
V in each case independently represents S, NH or O.

Those compounds of Formula I are particularly preferred in which in each case independently of each other
A represents an m-valent linear or branched aliphatic or aromatic $C_2$-$C_{20}$ radical, in particular a $C_4$-$C_{18}$ radical, preferably a $C_8$-$C_{16}$ radical and particularly preferably a $C_{10}$-$C_{14}$ radical, which can be interrupted by —O—, —CO—O—, —O—CO—, —CO—$NR^3$—, —$NR^3$—CO—, —O—CO—$NR^3$— or —$NR^3$—CO—O—, or represents an oligomeric group with a molar mass of from 400 to 1000 g/mol,
Q in each case independently is absent or represents an (n+1)-valent linear or branched aliphatic or aromatic $C_2$-$C_{15}$ radical, in particular a $C_3$-$C_{12}$ radical and preferably a $C_5$-$C_{10}$ radical, which can be interrupted by —O—, —CO—O—, —O—CO—, —CO—$NR^3$—, —$NR^3$—CO—, —O—CO—$NR^3$— or —$NR^3$—CO—O—, and particularly preferably represents —$CH_2$-phenylene-CO—O—$CH_2$—$CH_2$—,
Sp in each case independently represents a linear or branched aliphatic or aromatic $C_2$-$C_{20}$ radical, in particular a $C_4$-$C_{18}$ radical, preferably a $C_8$-$C_{16}$ radical and particularly preferably a $C_{10}$-$C_{14}$ radical, which can be interrupted by —O—, —CO—O—, —O—CO—, —CO—$NR^3$—, —$NR^3$—CO—, —O—CO—$NR^3$— or —$NR^3$—CO—O—, or represents an oligomeric group with a molar mass of from 400 to 1000 g/mol,
X in each case independently is absent or represents —O—, —CO—O—, —O—CO—, —CO—$NR^3$—, —$NR^3$—CO—, —O—CO—$NR^3$— or —$NR^3$—CO—O—,
Z in each case independently represents a polymerizable group selected from $CH_2$=$CR^1$—CO—O— and $CH_2$=$CR^1$—CO—$NR^2$—,
$R^1$, $R^2$ and $R^3$ in each case independently represent H or a $C_1$-$C_7$ alkyl radical, in particular H or a $C_1$-$C_5$ alkyl radical and preferably H or a $C_1$-$C_3$ alkyl radical,
$R^4$ in each case independently represents a $C_1$-$C_7$ alkyl radical, in particular a $C_1$-$C_5$ alkyl radical, preferably a $C_1$-$C_3$ alkyl radical and particularly preferably represents methyl, ethyl or isopropyl,
m can assume the values 2, 3 or 4 and is preferably 2,
n in each case independently can assume the values 1 or 2 and is preferably 1 and
p can assume the values 0, 1, 2 or 3, in particular 0 or 1, and is preferably 0.

In particular, such compounds of Formula I are preferred in which in each case independently of each other
T is selected in each case independently from and
R in each case independently represents H or a $C_1$-$C_7$ alkyl radical, in particular H or a $C_1$-$C_5$ alkyl radical, preferably H or a $C_1$-$C_3$ alkyl radical and particularly preferably represents H.

Quite particularly, such compounds of Formula I are preferred in which in each case independently of each other
U represents S,
V represents S,
W is absent or represents $CH_2$ or O and
Y in each case independently represents heteroaryl or —$P(O)(OR^4)_2$ and in particular represents pyridyl or —$P(O)(OEt)_2$.

In each case, groups in which all the variables have one of the preferred meanings defined above are particularly preferred.

It was surprisingly found that the compositions according to the present invention which comprise at least one thermolabile polymerizable compound of Formula I can be radically polymerized to form network polymers very well which are storage-stable at room temperature, but show a considerable reversible thermal cleavage even at moderately increased temperatures of in particular less than 100° C. These compositions are therefore particularly suitable for the preparation of materials with self-healing or debonding-on-demand properties, especially for the preparation of polymerization resins and polymerizates such as adhesives, composites, stereolithographic materials, shaped parts, duromers and mounting and fixing elements as well as for the preparation of dental materials such as adhesives, cements and filling composites.

The compositions according to the present invention are suitable in particular for the preparation of polymerizates which have a half-value temperature of less than 120° C., in particular less than 110° C., preferably less than 100° C. and particularly preferably less than 90° C. The term half-value temperature indicates the temperature at which half of the thermolabile groups T comprised in a sample are present in cleaved form. The half-value temperature can be determined in particular by spectroscopic monitoring of the retro-Diels-Alder reaction by means of a spectrometer with temperature-adjustable sample holder at a heating rate of 10 K/min.

The thermolabile polymerizable compounds of Formula I according to the present invention can be prepared easily. Thus, the synthesis of hetero-Diels-Alder adduct groups according to the present invention (HDA adduct groups) can be effected according to the following general formula:

Specific Example

Reaction of a dithioester with cyclopentadiene:

Reacting compounds having bis(diene) units with dienophiles comprising polymerizable groups directly provides compounds of general formula I, such as e.g.:

Reaction of e.g. diene units which are functionalized with OH groups (e.g. furan derivative) and dienophiles (e.g. dithioester) directly provides HDA adducts, which can be oligomerized by reaction with suitable difunctional compounds, e.g. in the case of the OH-functionalized HDA adducts with diisocyanates or dicarboxylic acid derivatives, wherein an excess of HDA adducts is used for OH terminated oligomers:

By subsequent end-group functionalization of the multifunctional OH-terminated HDA adduct oligomers with polymerizable groups, the compounds of Formula I can then be obtained.

Suitable starting materials for the synthesis of the polymerizable di- or multifunctional Diels-Alder or hetero-Diels-Alder adducts of general formula I are suitable diene derivatives, which can in particular be derived from substituted butadiene-1,3, cyclopentadiene (Cp) or furan derivatives. The photoenol derivatives represent a particular class, as here the diene species is only formed in-situ. Photoenols can be prepared via a multi-step synthesis comprising oxidation (D. M. Bauer, A. Rogge, L. Stolzer, C. Barner-Kowollik, L. Fruk, *Chem. Commun.* 2013, 49, 8626-8628), ether cleavage (K. K. Oehlenschlaeger, J. O. Mueller, N. B. Heine, M. Glassner, N. K. Guimard, G. Delaittre, F. G. Schmidt, C. Barner-Kowollik, *Angew. Chem. Int. Ed.* 2013, 52, 762-766), Williamson ether synthesis (D. M. Bauer, A. Rogge, L. Stolzer, C. Barner-Kowollik, L. Fruk, *Chem. Commun.* 2013, 49, 8626-8628) and a saponification (T. Pauloehrl, G. Delaittre, V. Winkler, A. Welle, M. Bruns, H. G. Börner, A. M. Greiner, M. Bastmeyer, C. Barner-Kowollik, *Angew. Chem. Int. Ed.* 2012, 51, 1071-1074). Many 1,3-butadiene derivatives are commercially available, such as 2,4-hexadien-1-ol or sorbic acid. Further derivatives can be synthesized by addition reactions (W. M. Gramlich, G. Theryo, M. A. Hillmyer, *Polym. Chem.* 2012, 3, 1510-1516) such as in the case of 2-methylenebut-3-en-1-ol or by substitution reactions (Y. Jing, V. V. Sheares, *Macromolecules* 2000, 33, 6255-6261) such as in the case of 3-methylene-4-penteneni-trile. Suitable Cp derivatives can be prepared for example by substitution reactions from the corresponding bromine-substituted derivatives with NaCp (S. Bian, A. M. Scott, Y. Cao, Y. Liang, S. Osuna, K. N. Houk, A. B. Braunschweig, *J. Am. Chem. Soc.* 2013, 135, 9240-9243) or NiCp$_2$ (M. Langer, J. Brandt, A. Lederer, A. S. Goldmann, F. H. Schacher, C. Barner-Kowollik, *Polym. Chem.* 2014, 5, 5330-5338). Cp derivatives such as (1-methyl-2,4-cyclopentadien-1-yl) methanol are commercially available. Commercially accessible furan derivatives are e.g. furfural, furfuryl alcohol or pyromucic acid (cf. Ullmann's Encyclopedia of Industrial Chemistry, 5th Ed. vol. A 12, VCH, Weinheim etc. 1989, 119 et seqq.). Substituted furan derivatives can be prepared by Paal-Knorr synthesis by heating corresponding 1,4-diketo compounds (cf. W. Walter, W. Francke, Beyer-Walter Lehrbuch der Organischen Chemie, S. Hirzel Verlag, Stuttgart and Leipzig 2004, 24th ed., p. 769).

For the synthesis of the polymerizable di- or multifunctional hetero-Diels-Alder adducts of Formula I, dienophile thioester derivatives, such as e.g. 4-((((diethoxyphosphoryl) carbonothioyl)thio)methyl)-benzoic acid or 4-(((pyridine-2-carbonothioyl)thio)methyl)-benzoic acid, which can be prepared via substitution reactions or salt metathesis (A. Alberti, M. Benaglia, M. Laus, K. Sparnacci, *J. Org. Chem.* 2002, 67, 7911-7914), are particularly suitable. Thioaldehydes which are formed by photochemical cleavage of phenacyl sulfides can likewise be used as dienophiles (M. Glassner, K. K. Oehlenschlaeger, A. Welle, M. Bruns, C. Barner-Kowollik, *Chem. Commun.* 2013, 49, 633-635). They can be prepared via the reaction of phenacyl bromides with thiols (G. A.-N. Gohar, S. N. Khattab, O. O. Farahat, H. H. Khalil, *J. Phys. Org. Chem.* 2012, 25, 343-350). In general, dienophiles with an electron-withdrawing group in conjugation to the double bond such as e.g. substituted maleimides (A. S. Quick, H. Rothfuss, A. Welle, B. Richter, J. Fischer, M. Wegener, C. Barner-Kowollik, *Adv. Funct. Mater.* 2014, 24, 3571-3580) are suitable for (hetero)-Diels-Alder reactions.

Hetero-Diels-Alder reactions typically take place using a catalyst such as e.g. ZnCl$_2$ (cf. M. Langer, J. Brandt, A. Lederer, A. S. Goldmann, F. H. Schacher, C. Barner-Kowollik, *Polym. Chem.* 2014, 5, 5330-5338) or TFA (A. J. Inglis, L. Nebhani, O. Altintas, F. G. Schmidt, C. Barner-Kowollik, *Macromolecules* 2010, 43, 5515-5520) or also without a catalyst (M. Glassner, G. Delaittre, M. Kaupp, J. P. Blinco, C. Barner-Kowollik, *J. Am. Chem. Soc.* 2012, 134, 7274-7277). Both organic solvents and water can be used as reaction medium.

Examples of the thermolabile polymerizable compounds of Formula I according to the present invention are:

-continued

-continued

The compositions according to the invention preferably comprise, in addition to the thermolabile polymerizable compound of Formula I, one or more additional radically polymerizable monomers (comonomers), in particular mono- or polyfunctional (meth)acrylic acid derivatives. By monofunctional (meth)acrylic acid derivatives is meant compounds with one, by polyfunctional (meth)acrylic acid derivatives are meant compounds with two or more, preferably 2 to 4 (meth)acrylic acid groups. Polyfunctional monomers have a cross-linking effect.

Preferred mono- or polyfunctional (meth)acrylic acid derivatives according to the present invention are methyl, ethyl, hydroxyethyl, butyl, benzyl, tetrahydrofurfuryl or isobornyl (meth)acrylate, bisphenol A di(meth)acrylate, bis-GMA (an addition product of methacrylic acid and bisphenol A diglycidyl ether), UDMA (an addition product of 2-hydroxyethyl methacrylate (HEMA) and 2,2,4-trimethyl-hexamethylene diisocyanate), di-, tri- or tetraethylene glycol di(meth)acrylate, trimethylolpropane tri(meth)acrylate, pentaerythritol tetra(meth)acrylate, glycerol di(meth)acrylate, 1,4-butanediol di(meth)acrylate, 1,10-decanediol di(meth)acrylate and 1,12-dodecanediol di(meth)acrylate.

Particularly preferred mono- or polyfunctional (meth)acrylic acid derivatives are N-mono- or -disubstituted acrylamides, such as N-ethylacrylamide, N,N-dimethacrylamide, N-(2-hydroxyethyl)acrylamide or N-methyl-N-(2-hydroxyethyl)acrylamide, N-monosubstituted methacrylamides such as N-ethylmethacrylamide or N-(2-hydroxyethyl)methacrylamide as well as N-vinylpyrrolidone and allyl ether. These monomers are characterized by a high hydrolysis stability and are particularly suitable as diluting monomers because of their relatively low viscosity.

Preferred polyfunctional (meth)acrylic acid derivatives with high hydrolysis stability are cross-linking pyrrolidones such as 1,6-bis(3-vinyl-2-pyrrolidonyl)-hexane, bisacrylamides such as methylene or ethylene bisacrylamide and bis(meth)acrylamides such as N,N'-diethyl-1,3-bis(acrylamido)-propane, 1,3-bis(methacrylamido)-propane, 1,4-bis(acrylamido)-butane or 1,4-bis(acryloyl)-piperazine which can be synthesized by reacting the corresponding diamines with (meth)acrylic acid chloride.

The compositions according to the present invention can also comprise further thermolabile cross-linking monomers as comonomers. Thermolabile cross-linking monomers have at least one thermolabile group between two polymerizable groups. Examples are polyfunctional (meth)acrylates or (meth)acrylamides with at least one thermolabile group between two (meth)acrylic groups. In particular thermolabile alkoxyamine, oxime-ester, oxime-urethane or azo groups, peroxides and disulfones come into consideration as thermolabile groups. Examples are the reaction products of N-hydroxy-(meth)acrylamide with di- or triisocyanates such as hexamethylene-1,6-diisocyanate (HDI), 2,2,4-trimethylhexamethylene-1,6-diisocyanate or the HDI trimer, as well as products which are obtained by stoichiometric reaction of di- or triisocyanates with 1-hydroxymethylacrylic acid esters such as 1-hydroxymethyl ethyl acrylate or with 3-keto ester (meth)acrylates such as 2-acetoacetoxyethyl methacrylate. Gas-releasing thermolabile cross-linking monomers are also particularly suitable. Examples are the esterification products of azobis(4-cyanovaleric acid) with hydroxyalkyl (meth)acrylates such as hydroxyethyl (meth)acrylate or hydroxypropyl (meth)acrylate or with N-(hydroxyalkyl) (meth)acrylamides such as N-(5-hydroxypentyl)methacrylamide or N-methyl-N-(2-hydroxyethyl)acrylamide.

In addition to the thermolabile polymerizable compound of Formula I and optionally the above-named comonomers, the compositions according to the present invention can preferably also comprise radical chain-transfer active additives which influence the structure of the polymerizates, in particular molar mass, molar mass distribution, network density, and make it possible to adjust properties such as glass transition temperature, width of the glass transition, impact strength and fracture toughness. Preferred radical chain-transfer active additives are dithioesters, tri-thiocarbonates, allyl sulfones, vinyl sulfone esters or other known RAFT reagents (RAFT=Reversible Addition-Fragmentation Chain Transfer).

In addition to the thermolabile polymerizable compound of Formula I and optionally the above-named comonomers, the compositions according to the present invention can preferably also comprise radically polymerizable, acid group-containing monomers (adhesive monomers). Preferred acid groups are carboxylic acid groups, phosphonic acid groups, phosphoric acid groups and sulfonic acid groups.

Preferred monomers with polymerizable carboxylic acids are maleic acid, acrylic acid, methacrylic acid, 2-(hydroxymethyl)acrylic acid, 4-(meth)acryloyloxyethyltrimellitic anhydride, 10-methacryloyloxydecylmalonic acid, N-(2-hydroxy-3-methacryloyloxypropyl)-N-phenylglycine and 4-vinylbenzoic acid.

Preferred monomers with polymerizable phosphonic acid groups are vinyl phosphonic acid, 4-vinylphenyl phosphonic acid, 4-vinylbenzyl phosphonic acid, 2-methacryloyloxyethyl phosphonic acid, 2-methacrylamidoethyl phosphonic acid, 4-methacrylamido-4-methyl-pentyl phosphonic acid, 2-[4-(dihydroxyphosphoryl)-2-oxa-butyl]-acrylic acid, 2-[4-(dihydroxyphosphoryl)-2-oxa-butyl]-acrylic acid ethyl and -2,4,6-trimethylphenyl ester.

Preferred monomers with polymerizable phosphoric acid groups are 2-methacryloyloxypropyl mono- or dihydrogen phosphate, 2-methacryloyloxyethyl mono- or dihydrogen phosphate, 2-methacryloyloxyethylphenyl hydrogen phosphate, dipentaerythritolpentamethacryl-oyloxy phosphate, 10-methacryloyloxydecyl dihydrogen phosphate, phosphoric acid mono-(1-acryloyl-piperidin-4-yl)-ester, 6-(methacrylamido)hexyl dihydrogen phosphate and 1,3-bis-(N-acryloyl-N-propylamino)-propan-2-yl-dihydrogen phosphate.

Preferred monomers with polymerizable sulfonic acid groups are vinylsulfonic acid, 4-vinylphenylsulfonic acid and 3-(methacrylamido)propylsulfonic acid.

Preferably, mixtures of the above-named monomers are used. Preferred monomer mixtures comprise, relative to the total weight of the monomer mixture:

1 to 90 wt.-%, preferably 5 to 80 wt.-%, particularly preferably 5 to 70 wt.-% compound of Formula I,
0 to 70 wt.-%, preferably 1 to 60 wt.-%, particularly preferably 5 to 50 and quite particularly preferably 10 to 30 wt.-% comonomer and in particular mono- and/or polyfunctional (meth)acrylates,
0 to 70 wt.-%, preferably 1 to 60 wt.-% and particularly preferably 5 to 50 wt.-% further thermolabile cross-linking monomer and
0 to 40 wt.-%, preferably 1 to 30 wt.-% and particularly preferably 5 to 20 wt.-% adhesive monomer.

Particularly preferred monomer mixtures (in each case relative to the total weight of the monomer mixture) are given in the following table:

| Component (wt.-%) | A | B | C | D | E | F |
|---|---|---|---|---|---|---|
| Compound of Formula I | 1-90 | 5-80 | 5-70 | 5-70 | 5-70 | 5-70 |
| Comonomer, in particular mono- and/or polyfunctional (meth)acrylate | 0-70 | 0-60 | 1-60 | 5-60 | 5-50 | 0-30 |
| Further thermolabile cross-linking monomer | 0-70 | 0-50 | 0-50 | 0-50 | 5-50 | 0-50 |
| Adhesive monomer | 0-40 | 0-30 | 0-30 | 0-20 | 0-20 | 0-30 |

Moreover, the compositions according to the present invention preferably also comprise an initiator for radical polymerization.

Preferably, benzophenone, benzoin and their derivatives or α-diketones or their derivatives, such as 9,10-phenanthrenequinone, 1-phenyl-propane-1,2-dione, diacetyl or 4,4'-dichlorobenzil are used to initiate radical photopolymerization, in particular in the case of thermolabile compounds of Formula I. Camphorquinone and 2,2-dimethoxy-2-phenyl-acetophenone are particularly preferably used as reducing agents, and quite particularly preferably α-diketones combined with amines, such as 4-(dimethylamino)-benzoic acid esters, N,N-dimethylaminoethyl methacrylate, N,N-dimethyl-sym.-xylidine or triethanolamine. Norrish type I photoinitiators, in particular acyl or bisacylphosphine oxides, monoacyltrialkyl- or diacyldialkylgermanium compounds, such as benzoyltrimethyl-germanium, dibenzoyldiethylgermanium or bis-(4-methoxybenzoyl)diethylgermanium are also particularly suitable. Mixtures of the different photoinitiators can also be used, such as for example dibenzoyldiethylgermanium combined with camphorquinone and ethyl 4-dimethylaminobenzoate.

Preferably, redox-initiator combinations, such as for example combinations of benzoyl peroxide with N,N-dimethyl-sym.-xylidine or N,N-dimethyl-p-toluidine, are used as initiators for a polymerization carried out at room temperature. Furthermore, redox systems consisting of peroxides and such reducing agents, such as e.g. ascorbic acid, barbiturates or sulfinic acids, are particularly suitable.

The compositions according to the present invention can additionally comprise a thermally gas-releasing additive. Suitable gas-releasing additives are e.g. azo compounds such as azodicarbonamide, 2,2'-azobisisobutyronitrile or 2,2'-azobis(4-cyanopentanoic acid), N-nitroso compounds, hydrazides such as benzenesulfonyl hydrazide, peroxides such as dicumol peroxide or acetone dicarboxylic acid. Examples of such compounds are described, for instance, in St. Quinn, *Plastics, Additives & Compounding* 2001, 3, 16-21. The decomposition temperature, for example in the case of azo compounds, can be adjusted by the substituent pattern in a manner known per se (cf. D. Braun, R. Jakobi, *Monatshefte Chemie* 1982, 113, 1403-1414).

Furthermore, the compositions according to the present invention can comprise an additive which can convert radiated electromagnetic radiation into heat. Such so-called radiation-to-heat converters are organic, inorganic or organometallic substances or hybrid components which are capable of converting UV, NIR or IR radiation, visible light, microwave or radiowave radiation into heat in order to cleave thermolabile groups. Examples of this are dyes and pigments that absorb UV, NIR or IR radiation. Examples of dyes that absorb in the IR range are azo, methine, anthraquinone or porphyrin dyes. Examples of pigments that absorb NIR radiation are antimony and indium tin oxide, phthalocyanine pigments, soot, Ni and Pt dithiolene complexes. Examples of compounds that absorb in the UV range are benzotriazoles, triazines, benzophenones, cyanoacrylates, salicylic acid derivatives and hindered amine light stabilizers (HALS). Examples of additives that absorb in the frequency range of microwaves (1 to 300 GHz) or radiowaves (10 kHz to 1 GHz) are ferromagnetic ceramic substances, so-called ferrites, which are composed of the iron oxides haematite ($Fe_2O_3$) or magnetite ($Fe_3O_4$) and further oxides for example of the metals Zn, Mn, or Ni and are commercially available as powders.

The compositions according to the present invention furthermore preferably also comprise organic or inorganic filler particles to improve the mechanical properties or to adjust the viscosity. Preferred inorganic particulate fillers are amorphous spherical materials based on oxides, such as $ZrO_2$ and $TiO_2$ or mixed oxides of $SiO_2$, $ZrO_2$ and/or $TiO_2$ with a mean average particle size of from 0.005 to 2 μm, preferably 0.1 to 1 μm, nanoparticulate or microfine fillers such as pyrogenic silica or precipitated silica with an average particle size of from 5 to 200 nm, preferably 10 to 100 nm, minifillers such as quartz, glass ceramic or glass powders with a mean average particle size of from 0.01 to 10 μm, preferably 0.1 to 1 μm, as well as radiopaque fillers such as ytterbium trifluoride or nanoparticulate tantalum(V) oxide or barium sulfate with a mean average particle size of from 10 to 1000 nm, preferably 100 to 300 nm.

Moreover, the compositions according to the present invention can comprise further additives, above all solvents such as water or ethanol or corresponding solvent mixtures as well as for example stabilizers, flavourings, dyes, microbiocidal active ingredients, fluoride-ion-releasing additives, optical brighteners or plasticizers.

Particularly preferred are compositions based on a thermolabile polymerizable compound of Formula I which comprise the following constituents:
a) 0.1 to 50 wt.-%, in particular 1 to 40 wt.-%, preferably 2 to 30 wt.-% and particularly preferably 5 to 30 wt.-% compound of Formula I,
b) 0.01 to 10 wt.-%, preferably 0.1 to 3.0 wt.-% and particularly preferably 0.2 to 2 wt.-% initiator,
c) 0 to 95 wt.-%, preferably 5 to 95 wt.-% and particularly preferably 5 to 90 wt.-% comonomer,
d) 0 to 10 wt.-%, in particular 0.1 to 5 wt.-% and preferably 0.2 to 3 wt.-% additive.

Filled polymerization resins and composites based on compounds of Formula I according to the present invention preferably comprise the following constituents:
a) 0.1 to 50 wt.-%, in particular 1 to 40 wt.-% and preferably 1 to 20 wt.-% compound of Formula I,
b) 0.01 to 10 wt.-% and in particular 0.1 to 3 wt.-% initiator,
c) 1 to 80 wt.-%, in particular 1 to 60 wt.-% and preferably 5 to 50 wt.-% comonomer,
d) 5 to 90 wt.-% and in particular 20 to 90 wt.-% filler,
e) 0 to 10 wt.-%, in particular 0.1 to 5 wt.-% and preferably 0.2 to 3 wt.-% additive.

Dental materials based on compounds of Formula I according to the present invention preferably comprise the following constituents:
a) 0.1 to 50 wt.-%, in particular 1 to 40 wt.-%, preferably 2 to 30 wt.-% and particularly preferably 5 to 30 wt.-% compound of Formula I,
b) 0.01 to 10 wt.-%, in particular 0.1 to 3.0 wt.-% and preferably 0.2 to 2 wt.-% initiator,
c) 0 to 80 wt.-%, in particular 1 to 60 wt.-% and preferably 5 to 50 wt.-% comonomer,
d) 0 to 80 wt.-% filler,
e) 0 to 70 wt.-% solvent and
f) 0 to 10 wt.-%, in particular 0.1 to 5 wt.-% and preferably 0.2 to 3 wt.-% additive.

The preferred filler content depends on the desired application. Adhesives preferably comprise 0 to 20 wt.-% and cements and composites preferably comprise 20 to 80 wt.-% filler.

This also applies to the solvent content. Adhesives preferably comprise 0 to 60 wt.-% and particularly preferably 1 to 50 wt.-% solvent. Compositions which comprise water as solvent are preferred. Compositions which comprise 0 to 20 wt.-% and in particular 1 to 10 wt.-% water are particularly preferred.

The debonding properties of compositions based on the compounds of Formula I according to the present invention can be influenced in a targeted manner by the composition of the materials. The adjustment of a composition suitable for a particular purpose belongs to the general knowledge and abilities of a person skilled in the art. The ability for debonding on demand by heating thus increases with the concentration of thermolabile components, i.e. of the compounds of Formula I and optionally further thermolabile cross-linkers or gas-releasing additives in the adhesive or cement. Furthermore, the debonding properties can also be modified by the choice of comonomers. The glass transition range and thus the softening range of the polymerizates can be influenced in a targeted manner by the choice of monomer. Moreover, the cross-linking density and thus also the strength and the elastic modulus can be modified with the ratio of cross-linking monomers or by addition of monofunctional monomers.

A subject of the invention is also the use of a polymerizable composition according to the present invention as dental material or for the preparation of a dental material, in particular an adhesive, cement or filling composite, as well as the use of a thermolabile polymerizable compound of Formula I for the preparation of dental materials, preferably adhesives, cements or filling composites and particularly preferably self-etching adhesives, cements or filling composites.

The compounds of Formula I according to the present invention can also be used for the preparation of materials with self-healing properties. By targeted tempering of such materials, the polymer network structure can be changed and stresses can be relieved or microcracks can be eliminated.

Furthermore, the compounds of Formula I can be used for the preparation of stereolithographic shaped bodies. Thus, stereolithographically prepared ceramic green bodies based thereon can demonstrate an improved debinding behaviour. In the case of stereolithographically constructed polymer or composite shaped bodies based on the compounds of Formula I according to the present invention, internal stresses can be relieved in a controlled manner by a heat treatment. Stereolithographically prepared wax models which comprise a polymer network based on the compounds of Formula I according to the present invention can be removed again in a simple manner in that the polymer network is degraded at increased temperature and the wax can then flow out. Furthermore, compounds of Formula I can be used for the preparation of chemically reversible mounting and fixing elements, for the reversible anchoring of materials or tools such as in particular dowels, anchors, screws, brackets or other connection elements in masonry, concrete, light construction or other structural elements.

A subject of the invention is therefore also the use of a polymerizable composition according to the present invention as polymerization resin, in particular as adhesive, composite or stereolithographic material, or for the preparation of a polymerizate, in particular of a shaped part, duromer, mounting or fixing element, and the use of a thermolabile polymerizable compound of Formula I for the preparation of a polymerization resin or polymerizate and in particular for the preparation of an adhesive, composite, stereolithographic material, shaped part, duromer or mounting or fixing element.

The invention is explained in more detail below by means of examples.

EXAMPLES

Example 1

Synthesis of bis-1,10-{10-(3-{4-[2-(methacryloyloxy)-ethoxycarbonyl]-benzylsulfanyl}-3-pyridin-2-yl-2-thia-bicyclo[2.2.1]hept-5-en-1-ylmethyl)}-decane 1st Step: 2-benzenesulfonylmethylpyridine

Sodium phenyl sulfinate (49.24 g, 0.30 mol), tetrapropylammonium bromide (10.64 g, 40.0 mmol) and 1,8-diazabicyclo[5.4.0]undec-7-ene (DABCO, 30.44 g, 0.20 mol) were added to a suspension of 2-(chloromethyl)pyridine hydrochloride (32.81 g, 0.20 mol) in acetonitrile (AN, 200 ml). The reaction mixture was heated under reflux for 16 h and then concentrated on a rotary evaporator. The residue was taken up in dichloromethane (DCM, 200 ml), washed with saturated aqueous NaCl solution (3×100 ml), dried over anhydrous Na$_2$SO$_4$, filtered and concentrated to approximately half the volume on a rotary evaporator. The brown solution was filtered over a layer of silica gel (SiO$_2$, ethyl acetate). 41.55 g (89% yield) 2-benzenesulfonylmethylpyridine were obtained as a yellowish solid.

¹H-NMR (400 MHz, CDCl₃: δ, ppm): 4.56 (s, 2H), 7.21-7.24 (m, 1H), 7.42-7.48 (m, 3H), 7.58-7.62 (m, 1H), 7.66-7.70 (m, 3H), 8.41-8.42 (m, 1H).

¹³C-NMR (101 MHz, CDCl₃, δ, ppm): 64.6, 123.4, 125.7, 128.4, 129.0, 133.8, 136.7, 138.2, 148.8, 149.7.

2nd Step: 4-(pyridine-2-carbothioylsulfanylmethyl)-benzoic Acid

A solution of DABCO (79.56 g, 0.523 mol) in AN (100 ml) was added dropwise to a suspension of 2-benzenesulfonylmethylpyridine (40.64 g, 0.174 mol) and sulfur (16.76 g, 0.523 mol) in AN (500 ml) accompanied by ice cooling. After the end of the addition, the dark red solution was stirred for 22 h at room temperature (RT), and then 4-(bromomethyl)-benzoic acid (37.46 g, 0.174 mol) was added in portions. The reaction mixture was stirred for a further 4 h at room temperature and then hydrochloric acid (2 N; 200 ml) was added (pH=1). The suspension was filtered. The filtration residue was washed with AN (100 ml). Methyl tert.-butyl ether (MtBE, 200 ml) and saturated aqueous NaCl solution (100 ml) were added to the filtrate and the phases were separated. The organic phase was washed with saturated aqueous NaCl solution (2×100 ml). The combined aqueous phases were re-extracted with MtBE (100 ml). The combined organic phases were dried over anhydrous Na₂SO₄, filtered and concentrated on a rotary evaporator. The residue was combined with the filtration residue obtained above, AN (200 ml) was added, and the mixture was stirred at RT. After 4 h the suspension was filtered. The filtration residue was washed with AN (50 ml) and dried in a vacuum drying cabinet (50° C., 125 mbar). 44.95 g (89% yield) 4-(pyridine-2-carbothioylsulfanylmethyl)-benzoic acid were obtained as a red solid.

¹H-NMR (400 MHz, CDCl₃: δ, ppm): 4.66 (s, 2H), 7.56-7.58 (m, 2H), 7.70-7.73 (m, 1H), 7.9-7.96 (m, 2H), 7.00-8.03 (m, 1H), 8.26-8.28 (m, 1H), 8.66-8.68 (m, 1H), 13.03 (s, 1H).

¹³C-NMR (101 MHz, CDCl₃, δ, ppm): 39.6, 121.9, 127.8, 129.4, 129.5, 129.9, 137.7, 140.6, 148.3, 155.3, 166.9, 226.0.

3rd Step: 4-(pyridine-2-carbothioylsulfanylmethyl)-benzoic acid-2-(methacryloyloxy)-ethyl Ester A suspension of 4-(pyridine-2-carbothioylsulfanylmethyl)-benzoic acid (10.39 g, 35.9 mmol), hydroxyethyl methacrylate (4.67 g, 35.9 mmol) and N,N-dimethylaminopyridine (DMAP, 0.60 g, 5.0 mmol) in DCM (100 ml) was cooled to 0° C. 3-(Ethyliminomethylidene-amino)-N,N-dimethyl-propane-1-aminehydrochloride (EDC.HCl, 8.26 g, 43.1 mmol) was added and the reaction mixture was stirred for 1 h at 0° C. and for 16 h at RT. The red reaction solution was filtered over a layer of silica gel (SiO₂, DCM) and the filtrate was concentrated on a rotary evaporator. n-Hexane (100 ml) was added to the oily red solid, and the mixture was stirred for 20 h at RT and filtered. The filtration residue was washed with n-hexane (50 ml) and dried in a vacuum drying cabinet (50° C., 125 mbar). 11.22 g (78% yield) 4-(pyridine-2-carbothioylsulfanylmethyl)-benzoic acid-2-(methacryloyloxy)-ethyl ester were obtained as a light red solid (mp: 80-81° C.).

¹H-NMR (400 MHz, CDCl₃: δ, ppm): 1.95 (s, 3H), 4.47-4.50 (m, 2H), 4.54-4.58 (m, 4H), 5.58-5.59 (m, 1H), 6.13-6.14 (m, 1H), 7.46-7.49 (m, 3H), 7.77-7.81 (m, 1H), 7.98-8.00 (m, 2H), 8.31-8.33 (m, 1H), 8.59-8.61 (m, 1H).

¹³C-NMR (101 MHz, CDCl₃, δ, ppm): 18.3, 40.8, 62.4, 62.7, 122.3, 126.2, 127.0, 129.0, 129.5, 130.0, 135.9, 137.0, 141.0, 148.0, 156.1, 166.0, 167.1, 225.4.

4th Step: 1,10-bis(cyclopentadienyl)-decane (DiCp-decane)

A sodium cyclopentadienide solution (2.0 M in THF, 100.0 ml, 0.20 mol) was added dropwise to a solution of dibromodecane (30.01 g, 0.10 mol) in anhydrous THF (400 ml) at −5° C. After the end of the addition, the cloudy brown solution was stirred further for 1 h at −5° C. and then at RT. After 20 h, the suspension was filtered over silica gel (SiO₂, ethyl acetate). The filtrate was concentrated on a rotary evaporator. The residue was dissolved in n-hexane (50 ml), filtered again over a layer of silica gel (SiO₂, n-hexane) and the filtrate was concentrated on a rotary evaporator. 22.64 g (84% yield) of a mixture of the isomers of 1,10-bis(cyclopentadienyl)decane were obtained as a colourless oil.

¹H-NMR (400 MHz, CDCl₃: δ, ppm): 1.22-1.34 (m, 12H), 1.46-1.58 (m, 4H), 2.29-2.42 (m, 4H), 2.79-2.96 (m, 4H), 5.95-6.46 (m, 6H).

¹³C-NMR (101 MHz, CDCl₃, δ, ppm): 29.0, 29.6, 29.6, 29.7, 29.8, 29.9, 30.0, 30.8, 41.2, 43.3, 125.7, 126.2, 130.4, 132.5, 133.6, 134.9, 147.5, 150.2.

5th Step: bis-1,10-{10-(3-{4-[2-(methacryloyloxy)-ethoxycarbonyl]-benzylsulfanyl}-3-pyridin-2-yl-2-thia-bicyclo[2.2.1]hept-5-en-1-ylmethyl)}-decane Hydrogen chloride (~1.25 M in methanol, 32.0 ml, 40.0 mmol) was added to a solution of 4-(pyridine-2-carbothio-ylsulfanylmethyl)benzoic acid-2-(methacryloyloxy)-ethyl ester (16.06 g, 40.0 mmol) in chloroform (80 ml) and stirred for 5 min at RT. A solution of 1,10-bis(cyclopentadienyl)-decane (5.41 g; 20.0 mmol) in chloroform (20 ml) was added dropwise and the reaction mixture was stirred at RT. After 20 h, the solution was washed with water (3×50 ml) and saturated aqueous $NaHCO_3$ solution (50 ml), dried over anhydrous $Na_2SO_4$, filtered and concentrated on a rotary evaporator. Purification by means of column chromatography ($SiO_2$, DCM/ethyl acetate) resulted in 16.82 g (78% yield) of a mixture of the isomers of bis-1,10-{10-(3-{4-[2-(methacryloyloxy)-ethoxycarbonyl]-benzylsulfanyl}-3-pyridin-2-yl-2-thia-bicyclo[2.2.1]hept-5-en-1-ylmethyl)}-decane as a yellowish oil.

$^1$H-NMR (400 MHz, $CDCl_3$: δ, ppm): 0.86-1.72 (m, 20H), 1.94 (s, 6H), 2.81-4.22 (m, 10H), 4.35-4.64 (m, 8H), 5.24-6.42 (m, 4H), 5.58 (s, 2H), 6.13 (s, 2H), 6.93-8.57 (m, 16H).

$^{13}$C-NMR (101 MHz, $CDCl_3$, δ, ppm): 18.3, 26.9, 28.7, 29.0, 29.1, 29.3, 29.5, 29.8, 29.9, 30.1, 33.5, 36.8, 37.2, 37.3, 49.7, 54.8, 56.5, 62.4, 62.5, 86.4, 121.4, 121.5, 124.9, 126.1, 126.2, 128.1, 128.9, 129.0, 129.0, 129.1, 129.6, 129.6, 135.9, 136.1, 136.3, 136.5, 143.7, 147.3, 152.9, 162.7, 166.1, 167.1.

Example 2

Synthesis of bis(2-(methacryloyloxy)ethyl)4,4'-(((1,1'-(decane-1,10-diyl)bis(3-(diethoxyphosphoryl)-2-thiabicyclo[2.2.1]hept-5-ene-3,1-diyl))bis(sul-fanediyl))bis(methylene))dibenzoate (DiHDA-linker)

1st Step: 4-(((((diethoxyphosphoryl)carbonothioyl)thio)methyl)-benzoic Acid (PDTMBA)

A solution of 5.3 ml diethyl phosphite (1.0 eq., 41 mmol, 5.7 g) in 40 ml anhydrous THF was added dropwise to a suspension of 1.5 g NaH (1.5 eq., 62 mmol) in 20 ml THF (dry) at RT. After the end of the $H_2$ formation, heating to boiling was carried out for 15 min. The reaction mixture was then cooled to −90° C. and 12.3 ml carbon disulfide ($CS_2$, 5.0 eq., 205 mmol, 15.6 g) were added dropwise. Stirring was carried out for 2 h at RT, during which the reaction mixture changed colour to brown. 750 ml THF were added. A solution of 10.0 g 4-bromomethylbenzoic acid (1.1 eq., 46 mmol) in 75 ml THF was then slowly added dropwise and stirring was carried out for 16 h at RT, wherein the reaction mixture changed colour to purple. After the solvent had been removed, the residue was taken up in a mixture of DCM and $H_2O$ (1:1). The organic phase was separated off and the aqueous phase was extracted with DCM. The combined organic phases were dried over anhydrous $Na_2SO_4$ and the solvent was removed. The product was then purified by means of column chromatography (silica gel 60, cyclohexane:ethyl acetate:acetic acid (1:1:0.01)). 4.3 g (30% yield) PDTMBA were obtained as a purple solid (mp: 113° C.).

$^1$H-NMR (400 MHz, $CDCl_3$: δ, ppm): 1.37 (t, 6H, $OCH_2CH_3$), 4.22-4.34 (m, 4H, $OCH_2CH_3$), 4.54 (s, 2H, $SCH_2$), 7.41 (d, 2H, ArH), 8.05 (d, 2H, ArH), 10.50 (bs, 1H, COOH).

$^{13}$C-NMR (101 MHz, $CDCl_3$, δ, ppm): 16.40 ($OCH_2CH_3$), 40.00 ($SCH_2$), 65.14 ($OCH_2CH_3$), 129.34 ($C_{ar}$), 129.53 ($C_{ar}$), 130.79 ($C_{ar}$), 140.04 ($C_{ar}$), 170.73 (COOH), 226.92 (PC=S), 228.66 (PC=S).

2nd Step: 2-(methacryloyloxy)ethyl-4-(((((diethoxy-phosphoryl)carbonothioyl)thio)methyl)benzoate (MA-PDTMBA))

A solution of 2.2 g EDC-HCl (2.0 eq., 11.5 mmol) and 0.14 g DMAP (0.2 eq., 1.15 mmol) in DCM (dry) was added dropwise to a solution of 2.0 g PDTMBA (1.0 eq., 5.74 mmol) and 1.05 ml 2-hydroxyethyl methacrylate (HEMA, 1.5 eq., 8.61 mmol, 1.12 g) in DCM (dry) at RT. After 20 h of stirring, washing was carried out with NaHCO$_3$ solution and saline solution. Drying was then carried out over anhydrous Na$_2$SO$_4$ and the solvent was removed. The product was purified by means of column chromatography (silica gel 60, cyclohexane:EE (1:1)). 1.85 g (70% yield) MA-PDT-MBA were obtained as a purple liquid.

$^1$H-NMR (400 MHz, CDCl$_3$, δ, ppm): 1.37 (t, 6H, OCH$_2$CH$_3$), 1.90 (s, 3H, CH$_3$C$_{MA}$), 4.22-4.34 (m, 4H, OCH$_2$CH$_3$), 4.42-4.58 (m, 4H, OCH$_2$CH$_2$O), 4.52 (s, 2H, SCH$_2$), 5.55 (d, 1H, CCH$_{2,trans}$), 6.10 (d, 1H, CCH$_{2,cis}$), 7.37 (d, 2H, ArH), 7.98 (d, 2H, ArH).

$^{13}$C-NMR (101 MHz, CDCl$_3$, δ, ppm): 16.40 (OCH$_2$CH$_3$), 18.40 (C$_{MA}$CH$_3$), 40.00 (SCH$_2$), 62.60 (OCH$_2$CH$_2$O), 65.14 (OCH$_2$CH$_3$), 126.27 (CH$_2$C$_{MA}$), 129.48 (C$_{ar}$), 129.65 (C$_{ar}$), 130.28 (C$_{ar}$), 136.03 (CH$_{MA}$), 139.50 (C$_{ar}$), 165.90 (C$_{ar}$C=O), 167.26 (C$_{MA}$C=O), 227.18 (PC=S), 228.93 (PC=S).

4th Step: bis(2-(methacryloyloxy)ethyl)4,4'-(((1,1'-(decane-1,10-diyl)-bis(3-(diethoxyphosphoryl)-2-thiabicyclo[2.2.1]hept-5-ene-3,1-diyl))bis(sulfanediyl))bis(methylene))dibenzoate (DiHDA-linker)

0.59 g 1,10-DiCp-decane (from Example 1, 4th step, 1.0 eq., 2.17 mmol), 2.0 g MA-PDTMBA (2.0 eq., 4.34 mmol) and 30 mg ZnCl$_2$ (0.1 eq., 0.22 mmol) were dissolved in ethyl acetate and stirred for 30 min at RT. Washing was then carried out with water and the solvent was removed. 2.56 g (99% yield) of the DiHDA-linker were obtained as a colourless, highly viscous liquid.

$^1$H-NMR (400 MHz, CDCl$_3$, δ, ppm): 1.25-1.65 (m, 28H, OCH$_2$CH$_3$, C$_{HDA}$CH$_2$(CH$_2$)$_4$), 1.94 (s, 6H, CH$_3$C$_{MA}$), 1.95-2.18 (m, 4H, CH$_{2,HDA-bridge}$), 2.18-2.50 (m, 4H, C$_{HDA}$CH$_2$(CH$_2$)$_4$), 3.35-3.68 (m, 2H, CH$_{HDA}$), 4.00-4.25 (m, 8H, OCH$_2$CH$_3$), 4.26-4.44 (m, 4H, SCH$_2$C$_{ar}$), 4.45-4.58 (m, 8H, OCH$_2$CH$_2$O), 5.52-5.60 (m, 1H, CH$_{HDA-Db}$), 5.58 (d, 2H, CCH$_{2,trans}$), 5.95-6.03 (2H, CH$_{HDA-Db}$), 6.13 (d, 2H, CCH$_{2,cis}$), 6.28-6.33 (m, 1H, CH$_{HDA-Db}$), 7.42 (d, 4H, ArH), 7.95 (d, 4H, ArH). MS: 1190.37 Da.

Example 3

Preparation of a Photopolymerizate of the DiHDA-Linker and Spectroscopic Monitoring of the Reversible Thermal Cleavage of the HDA Groups 0.2 wt.-% Ivocerin (bis-(4-methoxybenzoyl)-diethylgermanium) as photoinitiator was added to the DiHDA-linker prepared in Example 2, filled into a UV/Vis cuvette having a layer thickness of 1 mm and was polymerized by irradiation (30 min) with 3 Osram Dulux Blue lamps (3×18 W, >200 mW/cm$^2$). Absorption spectra in the range of 400-800 nm were then recorded at temperatures of from 25 to 140° C. of the formed polymer network using a Cary 300 Bio Spectrometer with a temperature-adjustable sample holder. The rate of the retro-hetero-Diels-Alder reaction (retro-HDA reaction) calculated from the absorption at the maximum at 530 nm in the temperature range of from 25 to 140° C. is represented in FIG. 1.

Figure 1:
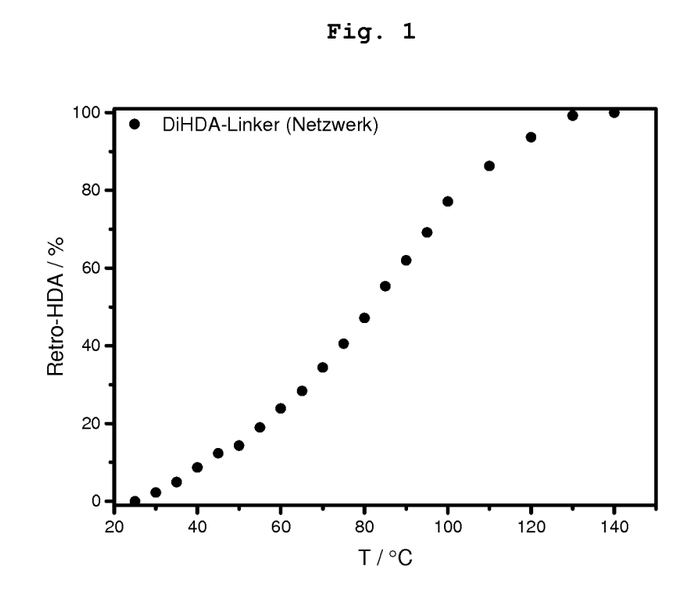
FIG. 1 shows in quantitative terms the breaking up of the polymer network as a function of the temperature based on the Vis-spectroscopically detected restitution of the coloured dithioester unit through the retro-HDA reaction.

FIG. 1 shows in quantitative terms the breaking up of the polymer network as a function of the temperature based on the Vis-spectroscopically detected restitution of the coloured dithioester unit through the retro-HDA reaction. Here the absorption in the visible range of the spectrum (Abs.$_{max}$: 530 nm) increases as the temperature rises until it reaches a maximum at 130° C., which demonstrates that the course of the retro-HDA reaction is complete. At 25° C. no absorption can be detected in the visible range of the spectrum, which indicates that the equilibrium of the HDA reaction at this temperature lies completely on the side of the completed HDA form. The fact that only the completed form is present at room temperature could also be proven by means of $^1$H-NMR spectroscopy of the DiHDA-linker. Because of the observation that the equilibrium of the HDA reaction at 25° C. lies 0% and at 130° C. lies 100% on the side of the retro HDA products, for any temperature in this range the degree of retro reaction can be given and the half-value temperature is at approx. 80° C. (cf. FIG. 1).

Example 4

Figure 2:
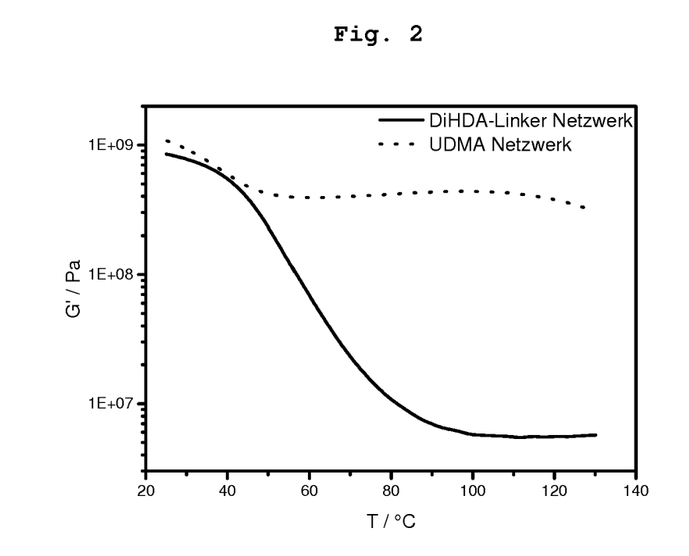
FIG. 2 shows behavior of a DiHDA-linker polymer network and a UDMA network at increasing temperature.

Preparation of a Photopolymerizate of the DiHDA-Linker and the Dynamic Mechanical Characterization Thereof From the DiHDA-linker prepared in Example 2, after addition of 0.2 wt.-% Ivocerin as photoinitiator, test pieces with the dimensions L: 25 mm, W: 5 mm, H: 1 mm were prepared by irradiation (30 min) with 3 Osram Dulux Blue lamps (3×18 W, >200 mW/cm$^2$). As a reference sample, analogous test pieces made from urethane dimethacrylate UDMA were prepared with addition of 0.2 wt.-% Ivocerin as photoinitiator and subsequent irradiation. The storage modulus G' of the prepared samples was measured by means of an ARES-G2 Rheometer (TA Instruments), which is a rotational rheometer with strain control. The rheometer has a force rebalance transducer, which makes possible torques between 50 nN·m and 200 mN·m with an accuracy of 1 nN·m. The oscillation frequency applied can be varied between 10$^{-7}$ rad/s and 628 rad/s. For temperature control, a convection oven with nitrogen supply was used. The temperature-dependent measurements were carried out with an axial force of 0.3 N, an excitation frequency of 1 Hz and a deformation of 0.1% in a temperature range of from 25 to 130° C. (heating rate: 1.5 K/min) and the G' results for the polymer networks of the DiHDA-linker and UDMA are represented in FIG. 2. G' represents the flow resistance of a substance and is thus a measure for the firmness of a material. As represented in FIG. 2, the DiHDA-linker polymer network and the UDMA network show a very different behaviour at increasing temperature. The storage modulus G' of the UDMA network shows only a slight decrease in the range of from 25 to 130° C., as is to be expected for non-thermally responsive networks ($1.1 \cdot 10^3$ MPa at 25° C. to $3.8 \cdot 10^2$ MPa at 120° C.). On the other hand, in the same temperature range, G' for the DiHDA-linker network decreases drastically from $8.5 \cdot 10^2$ MPa at 25° C. to 5.5 MPa at 120° C., which corresponds to a clear cleavage of the network. It can thus be shown that based on the polymerizable multifunctional hetero-Diels-Alder adducts of the general formula I, polymer networks are accessible which can be thermally reversibly degraded at temperatures clearly below 100° C.

Example 5

Figure 3:
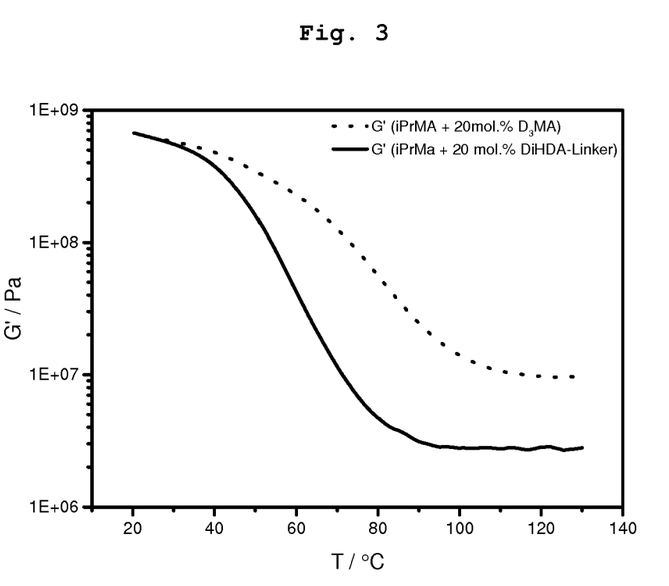
FIG. 3 shows a comparison of the storage modulus G' of a network from iPMA and a dimethacrylate $D_3MA$ with a network from iPMA and a DiHDA-linker.

Preparation of a Photocopolymerizate of the DiHDA-Linker and the Dynamic Mechanical Characterization Thereof The DiHDA-linker (20 mol-%) prepared in Example 2 was mixed with isopropyl methacrylate (iPMA). After addition of 0.2 wt.-% Ivocerin as photoinitiator, test pieces with the dimensions L: 25 mm, W: 5 mm, H: 1 mm were prepared by irradiation (30 min) with 3 Osram Dulux Blue lamps (3×18 W, >200 mW/cm$^2$). As a reference sample, analogous test pieces were prepared from a mixture of the commercially available cross-linker decanediol dimethacrylate (D$_3$MA) and iPMA (80 mol-%) with addition of 0.2 wt.-% Ivocerin as photoinitiator and subsequent irradiation. The storage modulus G' was measured as in Example 4. FIG. 3 shows the comparison of the storage modulus G' of a network from iPMA and the dimethacrylate D$_3$MA with a network from iPMA and the DiHDA-linker. The storage modulus G' of the D$_3$MA-iPMA network shows a considerable decrease in the range of from 25 to 130° C. due to the high proportion of the flexible monomethacrylate iPMA. Nevertheless, G' for the DiHDA-linker-iPMA network, which only comprises 20 mol-% of thermally reversible degradable DiHDA-linker, decreases significantly more clearly in the same temperature range.

Example 6

Cementation of Tooth Crowns with a Peroxide-Amine Initiated 2-Component Cement Based on the DiHDA-Linker from Example 2

Test abutments (geometry of a truncated cone, diameter of top surface: 4 mm, diameter of base surface: 6 mm, height: 3 mm) were milled from zirconium dioxide. To fit these, crowns were milled from zirconium dioxide such that a cement gap of 0.2 mm resulted when the crown was placed on the shoulder of the test abutment. Crowns and abutments were in each case sandblasted (110 μm Al$_2$O$_3$, 1 bar), cleaned with ultrasound in deionized water for approx. 2 min, dried and then prepared for the cementation with Monobond Plus (Ivoclar Vivadent AG, processing according to instructions for use: apply, leave to work for 60 s, blow dry with oil-free air).

For cementation, a self-curing two-component cement (mixing ratio 1:1 w/w) comprising 20 mol % (relative to the monomer mixture) of the thermally cleavable difunctional cross-linker DiHDA from Example 2 (cement A) was mixed. The first component comprised 25.06 wt.-% n-butyl methacrylate (BuMA), 0.01 wt.-% 2,6-di-tertbutyl-p-cresol (BHT), 60.35 wt.-% DiHDA-linker and 14.58 wt.-% BP-50-FT (50% dibenzoyl peroxide, United Initiators) as peroxide. The second component comprised 33.33 wt.-% BuMA, 63.67 wt.-% DiHDA-linker and 3 wt.-% 3,5-di-tert-butyl-N,N-diethylaniline (DABA). The quantities of BP-50-FT and DABA were chosen such that a processing time of approx. 1 to 5 min resulted.

As a comparison, a self-curing two-component cement (mixing ratio 1:1 w/w) comprising 20 mol % (relative to the monomer mixture) of the non-thermally cleavable difunctional cross-linker bisphenol A glycidyl methacrylate (bis-GMA) (cement B) was mixed analogously. The first component comprised 47.90 wt.-% BuMA, 47.10 wt.-% bisGMA and 5 wt.-% BP-50-FT. The second component comprised 54.30 wt.-% BuMA, 42.70 wt.-% bisGMA and 3 wt.-% DABA.

In each case two drops of the mixed cement were placed into a prepared test crown and the likewise prepared test abutment was put on top. After loading with a weight of approx. 2 kg, the cement excess was removed with a cotton pellet. After 10 min, the test crown and test abutment were unloaded and stored for 3 days at 23±2° C. In total, 10 crowns were thus cemented with cement A and 10 crowns with cement B.

To investigate the detachability, the 10 test pieces cemented with cement A and the 10 test pieces cemented with cement B were in each case randomly divided into two equally sized groups of 5 test pieces each and immersed for 1 min in water tempered to 23° C. (first group) or 80° C. (second group). The test pieces were then in each case clamped in a universal tensile testing machine (Zwick-Roell Z010), the crowns were pulled off the abutment with a constant traverse speed of 1.0 mm/min and the respective maximum force arising was registered as the pull-off force. The average of the thus-obtained pull-off force is represented in each case in the following table.

|  | Cement | |
| --- | --- | --- |
|  | Cement A (20 mol % DiHDA from Example 2; according to the present invention) | Cement B (20 mol % bis-GMA; comparison) |
| Pull-off force [N] after 1 min at 23° C. | 663 ± 184 | 962 ± 229 |
| Pull-off force [N] after 1 min at 80° C. | 42 ± 15 | 553 ± 171 |
| Percent reduction in the pull-off force through temperature increase from 23° C. to 80° C. | 94% | 42% |

These results show that only with the cement A according to the present invention based on the thermolabile DiHDA-linker from Example 2 is a practically complete debonding of the cemented crowns achieved even after one minute at 80° C.

The invention claimed is:
1. Polymerizable composition, which comprises a thermolabile polymerizable compound of Formula I:

Formula I, in which
A represents an m-valent linear, branched or cyclic aliphatic or aromatic $C_1$-$C_{30}$ radical which can be interrupted by —O—, —S—, —CO—O—, —O—CO—, —CO—NR$^3$—, —NR$^3$—CO—, —O—CO—NR$^3$—, —NR$^3$—CO—O— or —NR$^3$—CO—NR$^3$—, or represents an oligomeric group with a molar mass of from 200 to 2000 g/mol,
Q in each case independently is absent or represents an (n+1)-valent linear, branched or cyclic aliphatic or aromatic $C_1$-$C_{20}$ radical which can be interrupted by —O—, —S—, —CO—O—, —O—CO—, —CO—NR$^3$—, —NR$^3$—CO—, —O—CO—NR$^3$—, —NR$^3$—CO—O— or —NR$^3$—CO—NR$^3$—,
Sp in each case independently represents a linear, branched or cyclic aliphatic or aromatic $C_1$-$C_{30}$ radical which can be interrupted by —O—, —S—, —CO—O—, —O—CO—, —CO—NR$^3$—, —NR$^3$—CO—, —O—CO—NR$^3$—, —NR$^3$—CO—O— or —NR$^3$—CO—NR$^3$—, or represents an oligomeric group with a molar mass of from 200 to 2000 g/mol,
T is selected in each case independently from U in each case independently represents CH$_2$, S, NH or O,
V in each case independently represents CH$_2$, S, NH or O,
W in each case independently is absent or represents CH$_2$, O, S or NH,
X in each case independently is absent or represents —O—, —S—, —CO—O—, —O—CO—, —CO—NR$^3$—, —NR$^3$—CO—, —O—CO—NR$^3$—, —NR$^3$—CO—O— or —NR$^3$—CO—NR$^3$—,
Y in each case independently represents H, R$^4$, aryl, heteroaryl, —CN, —OR$^4$, —N(R$^4$)$_2$ or —P(O) (OR$^4$)$_2$,
Z in each case independently represents a polymerizable group selected from vinyl groups, CH$_2$=CR$^1$—CO—O— and CH$_2$=CR$^1$—CO—NR$^2$—,
one of the groups R represents a bond and the remaining groups R independently represent H or a linear or branched $C_1$-$C_9$ alkyl radical,
R$^1$, R$^2$ and R$^3$ in each case independently represent H or a linear or branched $C_1$-$C_9$ alkyl radical,
R$^4$ in each case independently represents a linear or branched $C_1$-$C_9$ alkyl radical,
m can assume the values 2 to 6,
n in each case independently can assume the values 1, 2 or 3 and
p can assume the values 0 to 10.
2. Composition according to claim 1, in which
U in each case independently represents S, NH or O and
V in each case independently represents S, NH or O.
3. Composition according to claim 1, in which
A represents an m-valent linear or branched aliphatic or aromatic $C_2$-$C_{20}$ radical, which can be interrupted by —O—, —CO—O—, —O—CO—, —CO—NR$^3$—, —NR$^3$—CO—, —O—CO—NR$^3$— or —NR$^3$—CO—O—, or represents an oligomeric group with a molar mass of from 400 to 1000 g/mol,
Q in each case independently is absent or represents an (n+1)-valent linear or branched aliphatic or aromatic $C_2$-$C_{15}$ radical, which can be interrupted by —O—, —CO—O—, —O—CO—, —CO—NR$^3$—, —NR$^3$—CO—, —O—CO—NR$^3$— or —NR$^3$—CO—O—,
Sp in each case independently represents a linear or branched aliphatic or aromatic $C_2$-$C_{20}$ radical, which can be interrupted by —O—, —CO—O—, —O—CO—, —CO—NR$^3$—, —NR$^3$—CO—, —O—CO—NR$^3$— or —NR$^3$—CO—O—, or represents an oligomeric group with a molar mass of from 400 to 1000 g/mol,
X in each case independently is absent or represents —O—, —CO—O—, —O—CO—, —CO—NR$^3$—, —NR$^3$—CO—, —O—CO—NR$^3$— or —NR$^3$—CO—O—,
Z in each case independently represents a polymerizable group selected from CH$_2$=CR$^1$—CO—O— and CH$_2$=CR$^1$—CO—NR$^2$—,
R$^1$, R$^2$ and R$^3$ in each case independently represent H or a $C_1$-$C_7$ alkyl radical,
R$^4$ in each case independently represents a $C_1$-$C_7$ alkyl radical,
m can assume the values 2, 3 or 4,
n in each case independently can assume the values 1 or 2 and
p can assume the values 0, 1, 2 or 3.
4. Composition according to claim 1, in which
T is selected in each case independently from R in each case independently represents H or a $C_1$-$C_7$ alkyl radical.
5. Composition according to claim 1, in which
U represents S,
V represents S,
W is absent or represents CH$_2$ and
Y in each case independently represents heteroaryl or —P(O) (OR$^4$)$_2$.
6. Composition according to claim 1, which comprises one or more additional radically polymerizable monomers comprising
methyl, ethyl, hydroxyethyl, butyl, benzyl, tetrahydrofurfuryl or isobornyl (meth)acrylate, bisphenol A di(meth)acrylate, bisGMA, UDMA, di-, tri- or tetraethylene glycol di(meth)acrylate, trimethylolpropane tri(meth)acrylate, pentaerythritol tetra(meth)acrylate, glycerol di(meth)acrylate, 1,4-butanediol di(meth)acrylate, 1,10-decanediol di(meth)acrylate, 1,12-dodecanediol di(meth)acrylate, and/or one or more N-mono- or -disubstituted acrylamides, N-ethylacrylamide, N,N-dimethacrylamide, N-(2-hydroxyethyl)acrylamide, N-methyl-N-(2-hydroxyethyl) acrylamide, one or more N-monosubstituted methacrylamides, N-ethylmethacrylamide, N-(2-hydroxyethyl) methacrylamide, N-vinylpyrrolidone, one or more cross-linking allyl ethers, and/or one or more cross-linking pyrrolidones, 1,6-bis(3-vinyl-2-pyrrolidonyl)-hexane, one or more cross-linking bisacrylamides, methylene or ethylene bisacrylamide, one or more cross-linking bis(meth)acrylamides, N,N'-diethyl-1,3-bis(acrylamido)-propane, 1,3-bis(methacrylamido)-propane, 1,4-bis(acrylamido)-butane, 1,4-bis(acryloyl)-piperazine, or a mixture thereof.

7. Composition according to claim 1, which comprises one or more radically polymerizable, acid group-containing monomers comprising maleic acid, acrylic acid, methacrylic acid, 2-(hydroxylmethyl)acrylic acid, 4-(meth)acryloyloxyethyltrimellitic anhydride, 10-methacryloyloxydecylmalonic acid, N-(2-hydroxy-3-methacryloyloxypropyl)-N-phenylglycine, 4-vinylbenzoic acid, and/or vinylphosphonic acid, 4-vinylphenylphosphonic acid, 4-vinylbenzylphosphonic acid, 2-methacryloyloxyethylphosphonic acid, 2-methacrylamidoethylphosphonic acid, 4-methacrylamido-4-methyl-pentyl-phosphonic acid, 2-[4-(dihydroxyphosphoryl)-2-oxa-butyl]-acrylic acid, 2-[4-(dihydroxyphosphoryl)-2-oxa-butyl]-acrylic acid ethyl- or -2,4,6-trimethylphenyl ester, and/or 2-methacryloyloxypropyl mono- or dihydrogen phosphate, 2-methacryloyloxyethylphenyl hydrogen phosphate, dipentaerythritol-pentamethacryloyloxyphosphate, 10-methacryloyloxydecyl dihydrogen phosphate, phosphoric acid mono-(1-acryloyl-piperidin-4-yl)-ester, 6-(methacrylamido)hexyl dihydrogen phosphate, 1,3-bis-(N-acryloyl-N-propyl-amino)-propan-2-yl dihydrogen phosphate, and/or vinylsulfonic acid, 4-vinylphenylsulfonic acid, 3-(methacrylamido)propylsulfonic acid, or a mixture thereof.

8. Composition according to claim 1, which comprises an initiator for radical polymerization.

9. Composition according to claim 1, which comprises a thermally gas-releasing additive.

10. Composition according to claim 1, which comprises an additive which can convert radiated electromagnetic radiation into heat.

11. Composition according to claim 1, which comprises organic and/or inorganic filler.

12. Composition according to claim 1, which comprises
a) 0.1 to 50 wt.-% compound of Formula I,
b) 0.01 to 10 wt.-% initiator,
c) 0 to 80 wt.-% comonomer,
d) 0 to 80 wt.-% filler,
e) 0 to 70 wt.-% solvent and
f) 0 to 10 wt.-% additive.

13. Composition according to claim 11, which comprises up to 20 wt.-% filler.

14. Composition according to claim 11, which comprises 20 to 80 wt.-% filler.

15. A dental material comprising the composition according to claim 1.

16. The dental material according to claim 15 for use as a polymerization resin, an adhesive, a composite, a stereolithographic material, a polymerizate, a shaped part, a duromer, a mounting or fixing element.

17. The dental material according to claim 15 for use as an adhesive, cement or filling composite.

18. Method of using a polymerizable composition, which comprises a thermolabile polymerizable compound of Formula I:

A-[X-(T-X-Sp-X)$_p$-T-X-Q-(Z)$_n$]$_m$  Formula I, in which

A represents an m-valent linear, branched or cyclic aliphatic or aromatic $C_1$-$C_{30}$ radical which can be interrupted by —O—, —S—, —CO—O—, —O—CO—, —CO—NR$^3$—, —NR$^3$—CO—, —O—CO—NR$^3$—, —NR$^3$—CO—O— or —NR$^3$—CO—NR$^3$—, or represents an oligomeric group with a molar mass of from 200 to 2000 g/mol, Q in each case independently is absent or represents an (n+1)-valent linear, branched or cyclic aliphatic or aromatic $C_1$-$C_{20}$ radical which can be interrupted by —O—, —S—, —CO—O—, —O—CO—, —CO—NR$^3$—, —NR$^3$—CO—, —O—CO—NR$^3$—, —NR$^3$—CO—O— or —NR$^3$—CO—NR$^3$—, Sp in each case independently represents a linear, branched or cyclic aliphatic or aromatic $C_1$-$C_{30}$ radical which can be interrupted by —O—, —S—, —CO—O—, —O—CO—, —CO—NR$^3$—, —NR$^3$—CO—, —O—CO—NR$^3$—, —NR$^3$—CO—O— or —NR$^3$—CO—NR$^3$—, or represents an oligomeric group with a molar mass of from 200 to 2000 g/mol, T is selected in each case independently from U in each case independently represents CH$_2$, S, NH or O, V in each case independently represents CH$_2$, S, NH or O, W in each case independently is absent or represents CH$_2$, O, S or NH, X in each case independently is absent or represents —O—, —S—, —CO—O—, —O—CO—, —CO—NR$^3$—, —NR$^3$—CO—, —O—CO—NR$^3$—, —NR$^3$—CO—O— or —NR$^3$—CO—NR$^3$—, Y in each case independently represents H, R$^4$, aryl, heteroaryl, —CN, —OR$^4$, —N(R$^4$)$_2$ or —P(O) (OR$^4$)$_2$, Z in each case independently represents a polymerizable group selected from vinyl groups, CH$_2$=CR$^1$—CO—O— and CH$_2$=CR$^1$—CO—NR$^2$—, one of the groups R represents a bond and the remaining groups R independently represent H or a linear or branched $C_1$-$C_9$ alkyl radical, R$^1$, R$^2$ and R$^3$ in each case independently represent H or a linear or branched $C_1$-$C_9$ alkyl radical, $R^4$ in each case independently represents a linear or branched $C_1$-$C_9$ alkyl radical, m can assume the values 2 to 6, n in each case independently can assume the values 1, 2 or 3 and p can assume the values 0 to 10 for the preparation of a polymerization resin, a polymerizate, an adhesive, a composite, a stereolithographic material, a shaped part, a duromer, a mounting element or a fixing element.

19. Composition according to claim 1, in which

A represents a $C_4$-$C_{18}$ radical, which can be interrupted by —O—, —CO—O—, —O—CO—, —CO—NR$^3$—, —NR$^3$—CO—, —O—CO—NR$^3$— or —NR$^3$—CO—O—, or represents an oligomeric group with a molar mass of from 400 to 1000 g/mol, Q in each case independently is absent or represents a $C_3$-$C_{12}$ radical, which can be interrupted by —O—, —CO—O—, —O—CO—, —CO—NR$^3$—, —NR$^3$—CO—, —O—CO—NR$^3$— or —NR$^3$—CO—O—, or —CH$_2$-phenylene-CO—O—CH$_2$—CH$_2$—, Sp in each case independently represents a linear or branched aliphatic or aromatic a $C_4$-$C_{18}$ radical, which can be interrupted by —O—, —CO—O—, —O—CO—, —CO—NR$^3$—, —NR$^3$—CO—, —O—CO—NR$^3$— or —NR$^3$—CO—O—, or represents an oligomeric group with a molar mass of from 400 to 1000 g/mol, X in each case independently is absent or represents —O—, —CO—O—, —O—CO—, —CO—NR$^3$—, —NR$^3$—CO—, —O—CO—NR$^3$— or —NR$^3$—CO—O—, Z in each case independently represents a polymerizable group selected from CH$_2$=CR$^1$—CO—O— and CH$_2$=CR$^1$—CO—NR$^2$—, $R^1$, $R^2$ and $R^3$ in each case independently represent H or a $C_1$-$C_5$ alkyl radical,

$R^4$ in each case independently represents a $C_1$-$C_5$ alkyl radical m can assume the values 2, 3 or 4, n in each case independently can assume the values 1 or 2 and p can assume the values 0, 1, 2 or 3.

20. Composition according to claim 1 in which T is selected in each case independently from and R in each case independently represents H, a $C_1$-$C_5$ alkyl radical.

21. Composition according to claim 1, in which

U represents S,

V represents S,

W is absent or represents CH$_2$ and

Y in each case independently represents pyridyl or —P(O)(OEt)$_2$.

22. Composition according to claim 1, which comprises a) 1 to 40 wt.-% compound of Formula I,
b) 0.1 to 3.0 wt.-% initiator,
c) 1 to 60 wt.-% comonomer,
d) 0 to 80 wt.-% filler,
e) 0 to 70 wt.-% solvent and
f) 0.1 to 5 wt.-% additive.

23. Composition according to claim 1, which comprises a) 2 to 30 wt.-% compound of Formula I,
b) 0.2 to 2 wt.-% initiator,
c) 5 to 50 wt.-% comonomer,
d) 0 to 80 wt.-% filler,
e) 0 to 70 wt.-% solvent and
f) 0.2 to 3 wt.-% additive.

24. Composition according to claim 3, in which $R^1$, $R^2$ and $R^3$ in each case independently represent H or a $C_1$-$C_5$ alkyl radical, m is 2, and n is 1.

25. Composition according to claim 19, in which

A represents a $C_8$-$C_{16}$ radical m is 2, n is 1.

* * * * *